United States Patent [19]

Scott

[11] Patent Number: 4,787,380
[45] Date of Patent: Nov. 29, 1988

[54] DELIVERY SYSTEM AND PACKAGE FOR A SELF ADHERING POLYMER MEDICAL DRESSING

[75] Inventor: David F. Scott, Sandy, Utah

[73] Assignee: Becton, Dickinson and Company, Franklin Lakes, N.J.

[21] Appl. No.: 90,497

[22] Filed: Aug. 28, 1987

[51] Int. Cl.⁴ .............................................. A61L 15/00
[52] U.S. Cl. .................................... 128/156; 128/155; 206/440; 206/441; 206/484; 206/484.1
[58] Field of Search ....................... 128/155, 156, 335; 604/307, 308, 897; 206/438, 440, 441, 484, 484.1; 428/94, 315.7

[56] References Cited

U.S. PATENT DOCUMENTS

| | | | |
|---|---|---|---|
| 1,920,808 | 8/1933 | Sander | 128/156 |
| 2,969,144 | 1/1961 | Zackheim | 128/156 |
| 3,425,412 | 2/1969 | Pope | 128/156 |
| 4,281,650 | 8/1981 | Spiegelberg | 128/156 |
| 4,641,643 | 2/1987 | Greer | 128/156 |
| 4,664,106 | 5/1987 | Snedeker | 128/156 |

FOREIGN PATENT DOCUMENTS 0090564 10/1983 European Pat. Off. ............ 128/155

Primary Examiner—Richard J. Apley
Assistant Examiner—Paul Prebilic
Attorney, Agent, or Firm—Aaron Passman

[57] ABSTRACT

The delivery system and package for a self adhering polymer medical dressing includes a film carrier and a siliconized release paper and a film backing sheet sandwiched therebetween. The film backing sheet has two parts; a dressing and a bounding area heat sealed to the film carrier. The dressing area being defined by a cut line just inside the heat sealed area. The sandwich forms a contamination barrier package. The adhesive coating and siliconized release paper form a barrier on that side of the dressing and the film carrier and the heat seal form a barrier package. The adhesive is on the other side of the dressing. A part of the cut line is perforated to resist separation of the dressing during removal of the siliconized release paper. The manufacturing method includes the steps of; transferring the release paper and adhesive to the film backing sheet, cutting the film backing sheet to define the dressing, heat sealing the film carrier about the edges of the cut line of the dressing and severing individual dressings.

8 Claims, 3 Drawing Sheets

DELIVERY SYSTEM AND PACKAGE FOR A SELF ADHERING POLYMER MEDICAL DRESSING

FIELD OF THE INVENTION

This relates to delivery systems useful in the application of thin film dressings for wounds or surgery, and the packaging for such dressings to prevent contamination of the part of the dressing which contacts a biological subject.

BACKGROUND AND ART IN THE FIELD OF THE INVENTION

Dressings for wounds and surgery are made of a variety of thin moisture vapor transmissive films as disclosed in U.S. Pat. Nos. 3,483,018 and 3,645,835. These dressings are used in many applications and are impervious to bacteria and liquid water, but permit ambient oxygen to penetrate the dressing and allow moisture vapor to escape from beneath the dressing. Healing of a dressed wound is enhanced while the injury is protected. To provide desired levels of moisture vapor transmission from beneath the dressing and oxygen transfer from outside the dressing very thin films of polyurethane or other polymers are used.

These thin films are typically less than 10 mils thickness wherefore they are flexible, limp and flimsy. Consequently, such films can easily be applied over the contours of a biological subject and can be worn in relative comfort. The application of these films requires a layer of permeable adhesive coating to secure the film to the subject when the film is used as a dressing. A release sheet is used to cover the adhesive coating and protect the dressing prior to application. Removal of the release sheet prior to dressing application leaves the film and adhesive coating in a difficult condition for handling, application and use. In particular, the thin flexible film and adhesive coating require a delivery system to prevent the dressing from adhering to itself during attempted application to a biological subject. Dressings have been made with various tabbed release sheets and frame supports as disclosed in U.S. Pat. Nos. 2,734,503, 3,260,260, 3,349,745, 4,372,303, 4,485,809, 4,664,106. These delivery arrangements help by providing support for the thin flexible film during the application of the dressing.

Contamination of the adhesive surface must be prevented during and prior to application of the thin film dressing. With any dressing of the type described an over package is usually provided in order to maintain the sterile barrier until the dressing and its delivery system are used. These over packages include a wrapper composed of a top and bottom forming an enclosure to protect the product from contamination until unwrapping and use. As with any disposable medical product, the wrapper is designed for easy opening such as peeling the top from the bottom so the dressing can be removed without contamination of the biological subject side of the dressing.

Dressings of the type described have unnecessary expense in manufacture because of the number of components used for assisting delivery and for preventing contamination before removal from the package for use. Dressings of the type described do not permit or facilitate accurate control and placement of the dressing because the delivery system fails to provide sufficient support of the thin film backing and adhesive coating combination. Dressings of the type described require needless additional packaging material and assembly operations for purposes of establishing a sterile barrier.

SUMMARY OF THE INVENTION

The present dressing eliminates difficulties in applying thin adhesively coated films to biological subjects. The dressing of the invention includes a transparent carrier film at least coextensive with the film backing sheet to reinforce and entirely support the film backing sheet during application of the adhesive coated side thereof to a biological subject. The carrier film is heat sealed to the edges of the film backing sheet to provide attachment and a sterility barrier on that side of the film backing sheet. On the other side of the film backing sheet placed over the adhesive coating is a siliconized release paper which together with the film carrier form a sandwich having the film backing sheet in the middle.

The film backing sheet is cut about its center portion to delimit the area of the dressing. In particular, the cut line is inside the heat sealed edges and thus demarcates the dressing portion of the film backing sheet. The sterile package is formed by the film carrier which protects the film backing sheet on one side and the release paper secured to and over the adhesive coating on the other side. As with an good package, the release paper includes indicia on the outwardly facing surface. The film carrier may also have selectively positioned indicia. Because of the bounding cut line which defines the dressing portion of the film backing sheet, the sterility of the dressing is protected from inward migration of contaminates between the layers of the sandwich.

The use of the dressing is quite simple in that the release paper is removed from the adhesive of the film backing sheet and the sheet supported on the film carrier is applied to a biological subject over a wound or I.V. catheter site. The transparent film carrier is used to support and handle the thin adhesively coated film backing sheet during application. After the adhesively coated film backing sheet is firmly adhered to the subject the film carrier can be removed taking with it the heat sealed connected edge portions which bound the demarcation of the dressing portion of the film backing sheet. This leaves the dressing firmly adhered to the biological subject. The edges of the dressing are completely uncontaminated as they have been demarcated by the cut line and enclosed in the sandwich formed by the film carrier and the release paper.

The process for manufacturing this delivery system and package includes an operation wherein the film backing sheet is adhesively coated by application to a siliconized release paper with the adhesive coating. Instructions are printed on the side of the release paper opposite where the silicone and adhesive are. The combination of the film backing sheet and the release paper is then passed under a knife edge die which cuts the boundary (demarcation line) for the dressing through the film backing sheet but not through the siliconized release paper. The transparent film carrier is then applied over the film backing sheet covering the dressing and the area bounding the dressing. That area is subsequently heat sealed just beyond the edges of the dressing outside the perimeter of the cut line. The heat sealing forms a contamination barrier for the dressing at the juncture of the film backing sheet and film carrier. The siliconized release paper forms a barrier on the adhesive coating side whereupon a sandwich is formed which captures therein the dressing and protects same from contamination.

OBJECTS OF THE INVENTION

It is an object of the present disclosure to teach the invention of a method of manufacture of a combination delivery system and package for a self adhering polymer medical covering having a minimum number of layers of material.

It is another object of the present disclosure to explain the inventive technique by which the film carrier can be connected to the film backing sheet for easy and convenient use during application.

It is still another object of the present disclosure to provide an inventive technique for the manufacture of the delivery system and package for a self adhering polymer medical covering consisting of a sandwich composed of a carrier film and a release paper with a thin flexible adhesively coated dressing protectively enclosed therebetween.

DETAILED DESCRIPTION OF THE DRAWINGS

Figure 1:
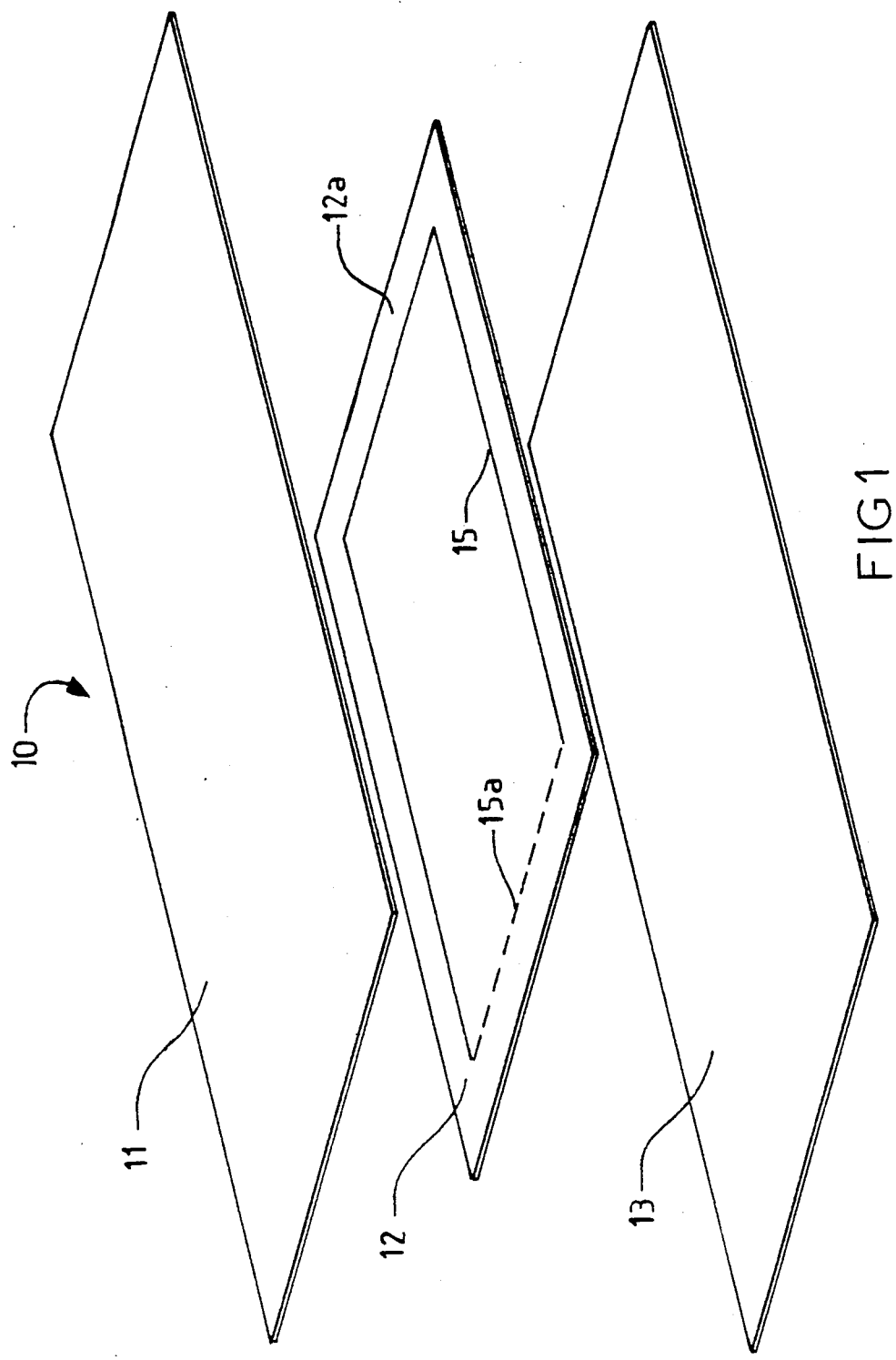
FIG. 1 is a exploded perspective view showing the components of the delivery system and package for a self adhering polymer medical dressing.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

The components of the self adhering polymer medical delivery system and package 10 are shown in the exploded perspective view in FIG. 1. There are three layers consisting of the film carrier 11, the film backing sheet 12 and the siliconized release paper 13. The film carrier can be any transparent plastic material which is heat sealable to the moisture vapor permeable film used for the film backing sheet 12. In the preferred embodiment the film carrier 11 is a Surlyn ® EVA transparent polymer material from DuPont and the film backing sheet 12 is a transparent polyurethane material. The polyurethane material is about one-half of a mil thick and is adhesively coated on the side opposite that to which the film carrier is heat sealed. The acrylic pressure sensitive adhesive coating is moisture vapor transmissive. The dimensions for a typical dressing include the film carrier 11 which is two inches by four inches and about four to six mils thick and the siliconized release paper 13 which is also two inches by four inches. The film backing sheet 12 is somewhat smaller in length being approximately two inches by three to three and one-half inches and is centered relative to the film carrier 11 and the siliconized release paper 13, see FIG. 2.

Figure 2:
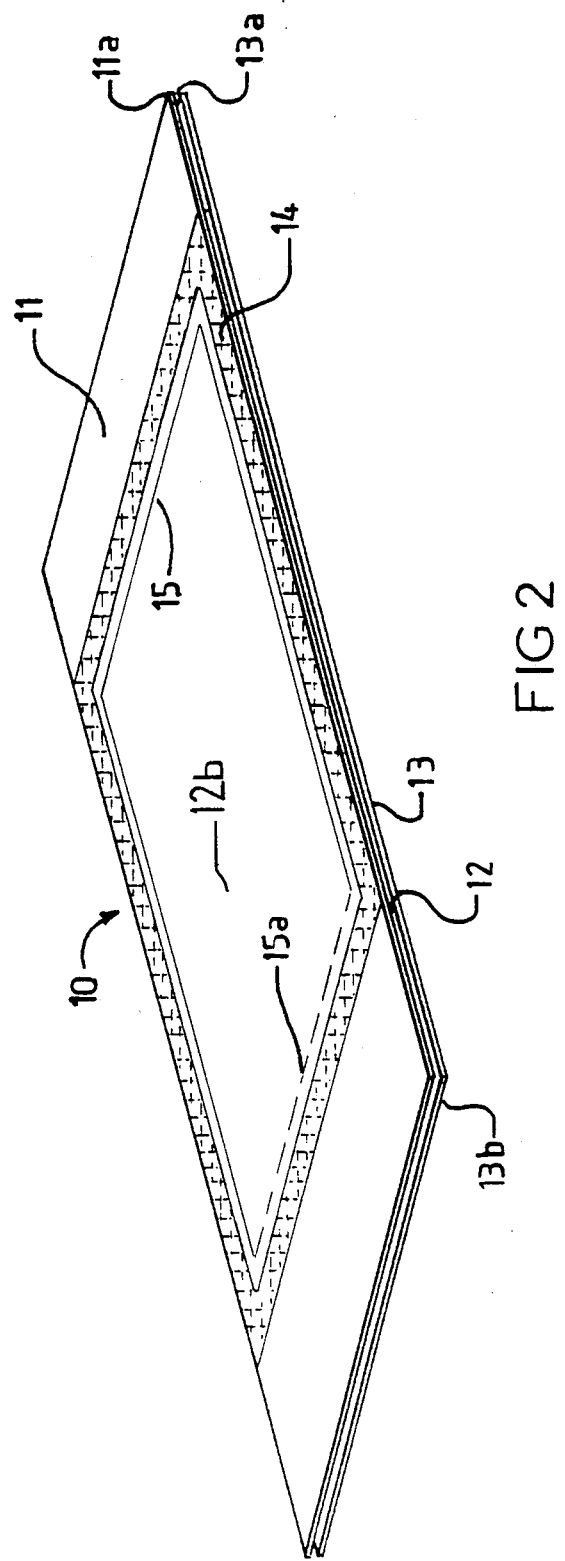
FIG. 2 is a perspective view of the delivery system and package for a self adhering polymer medical dressing as same would appear from the film carrier side thereof.

The self adhering polymer medical delivery system and package 10 is a sandwich formed by the combination of the components described and is shown in FIG. 2 where the heat sealed border is illustrated at bounding area 14. The self adhering polymer medical delivery system and package 10 includes the film carrier 11, the film backing sheet 12 and the siliconized release paper 13 arranged such that the film backing sheet 12 is centered longitudinally relative to the film carrier 11 and the siliconized release paper 13. As shown in both FIGS. 1 and 2, there is a cut line 15 just inside of the heat sealed bounding area 14. Cut line 15 is completely through the film backing sheet 12 except transverse portion 15a where the cut line is perforated. The perforated line of portion 15a is used to assist in the application of the dressing 12b defined by the cut line 15 such that the dressing 12b will not separate from the film backing sheet border portion 12a upon removal of the release paper 13.

In particular, when the dressing 12b is to be applied the siliconized release paper 13 is removed by peeling the paper away from the adhesive coating of the film backing sheet 12. This can easily be done by grasping the release paper 13 at end 13b, closest to the perforated cut line 15a, see FIG. 2. The perforated cut line 15a thus acts to resist peeling of the dressing 12b from the film carrier 11 during removal of the release paper 13. Once the release paper 13 has been peeled from the adhesive coating on the film backing sheet 12 the dressing 12b can be handled because the film carrier 11 supports the flimsy, limp and adhesively coated film backing sheet 12 at heat sealed area 14 near perforated cut line 15a and about the contacting portions of the mating surfaces of the film carrier 11 and film backing sheet 12 which are not heat sealed. The natural adherence between the surfaces of two flat clean plastic films, either by means of static charge or by means of exclusion of air, holds the dressing 12b to the film carrier 11. The combination is placed over a wound or an intravenous catheter site and can be easily positioned because of the transparency of the film carrier 11 and the film backing sheet 12.

After placement and adherence of the dressing 12b to the biological subject the end 11a of the film carrier 11 which is furthest from the perforated cut line 15a is peeled away from the dressing 12b which is adhered to the wound or site. The cut line 15 demarcates three sides of the dressing 12b which are easily separated from the film carrier 11 because the heat sealed area 14 connects the bounding area of the film backing sheet 12 to the film carrier 11. Inside the cut line 15, the natural adherence between the dressing 12b and the film carrier 11 is less than the connection in the heat sealed area 14 and is less than the adhesive tack of the adhesive coating on the film backing sheet 12. The application of the film carrier 11 and the dressing 12b over the wound or intravenous site will cause the dressing 12b to stick as the film carrier 11 is peeled back from edge 11a separating the adhering cut portion of the film backing sheet 12 leaving the dressing 12b attached to the biological subject as the film carrier 11 and heat sealed bounding area 14 are removed. When the removed film carrier has been peeled back to the perforated cut line 15a a greater amount of resistance exists between the film carrier and the cutout dressing portion of the film backing sheet 12. This greater resistance once useful in removal of the release paper 13, is now torn since the adhesively connected dressing 12b has sufficient area of contact with the wound or site to permit the film carrier 11 to be pulled with the force necessary to tear along the line of the perforations at portion 15a.

The self adhering medical polymer delivery system and package 10 as shown in FIG. 2 is clearly a sterile package. The actual dressing 12b is defined by the cut line 15 and the perforated cut line 15a. The film backing sheet is heat sealed to the film carrier 11 about the outside of the cut line 15 and the perforated cut line 15a. The dressing 12b is protected from contamination since the siliconized release paper 13 is adhesively adhered to the film backing sheet 12. Contamination cannot reach either side of the dressing 12b. Until such time as the siliconized release paper has been removed from the adhesive coating on the film backing sheet 12, the contamination barrier is adequate to maintain sterility. After removal of the release paper 13, the dressing 12b is easily handled by means of film carrier 11 without fear of contamination. The application of the dressing 12b is accomplished when the film carrier 11 and the heat sealed bounding area 14 are removed leaving the delivered dressing 12b applied to the biological subject. No over package of any type is required since the dressing 12b is completely protected from contamination by the sandwich of the film carrier 11 and the release paper 13.

Figure 3:
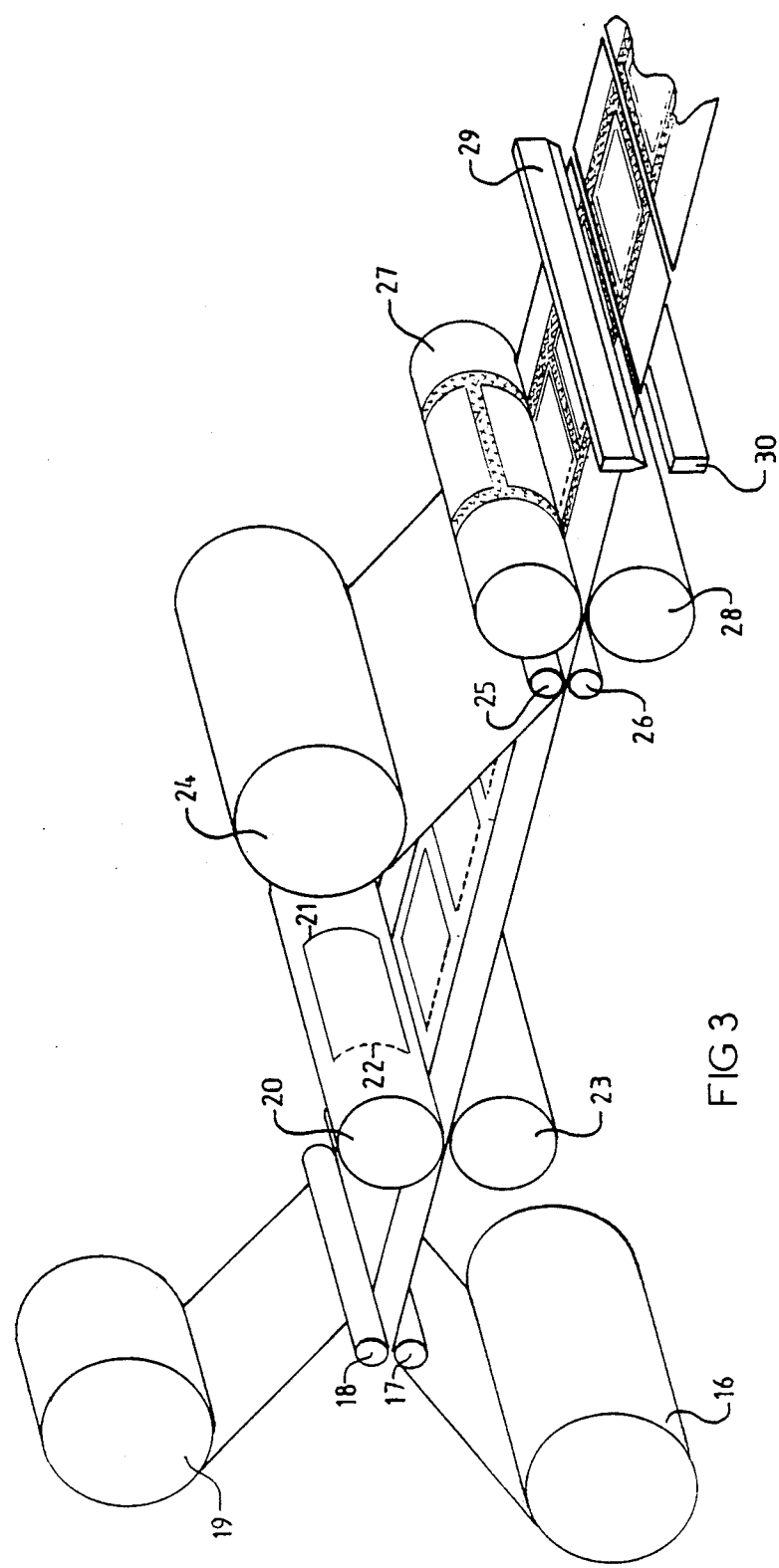
FIG. 3 is a schematic presentation of the manufacturing equipment and operational steps necessary to produce the delivery system and package for a self adhering polymer medical dressing.

FIG. 3 shows a schematic view of a simplified arrangement for the manufacture of the self adhering polymer medical delivery system and package 10, shown in FIG. 2. There is a roll 16 which supplies the siliconized release paper 13 carrying an acrylic adhesive coating to a pair of juxtaposed rollers 17 and 18. The polyurethane film backing sheet 12 is also delivered from supply roll 19 to the nip of rollers 17 and 18. The contact under the pressure of rollers 17 and 18 of the film backing sheet 12 and the acrylic adhesive coating side of the siliconized release paper 13 transfers the adhesive coating to the polyurethane film backing sheet 12.

From the nip of rollers 17 and 18 the material passes beneath a dressing cutting roller 20 having thereon knife blades 21 and 22 defining the cut line 15 and the transverse perforated cut line 15a respectively. A backup roller 23 is juxtaposed to cutting roller 20 to support the release paper side of the film backing sheet 12 as same passes between the nip of rollers 20 and 23. Roll 24 carries the transparent stock for the film carrier 11 and delivers film carrier for application over the film backing sheet 12. Juxtaposed rollers 25 and 26 press the film carrier 11 to the film backing sheet 12 excluding the air between the carrier and the sheet. The pressure of the nip of rollers 25 and 26 generates intimate surface contact of the adjoining polymer films forming the natural adherence therebetween.

From rollers 25 and 26 the sandwich of release paper 13, film backing sheet 12 and film carrier 11 continues to another pair of juxtaposed rollers 27 and 28. Roller 27 carries a heat sealer element positioned to attach the film carrier 11 to the film backing sheet 12 in the area about the cut line 15 and the transverse perforated cut line 15a. Thus the heat sealed boundary area 14 is generated by melting at the interface of the adjoining polymer films (between the film carrier and the film backing sheet). The heat sealer element fuses the films together to form a welded structure.

A knife blade 29 is used against a backup bar 30 in the next manufacturing step to sever individual dressings as shown in FIG. 3. Blade 29 and its backup bar 30 are positioned transverse to the direction of travel of the dressings whereby individual severed dressings are manufactured with each reciprocating stroke of the knife blade 29. While not shown it can be appreciated that the completed dressing as manufactured according to the arrangement of FIG. 3 can be stacked and placed in a dispenser container having a slot which facilitates the easy removal of an individual self adhering polymer medical dressing 10 for use as explained.

While a particular structure and manufacturing process have been shown and described, the invention which is covered in the claims which follow should not be limited to particular materials used or a specific geometry, size or manufacturing arrangement. The claims seek to cover the idea of a package and delivery system which prevent contamination before use and to allow the easy application of the dressing without contamination.

What is claimed is:

1. A delivery system and package for a self adhering polymer medical dressing for application over parts of biological subjects comprising:

a film backing sheet having a subject facing surface and an opposite outward surface defined by an edge and including a dressing demarcated by being substantially cut out of said film backing sheet and said dressing designed for application to a selected part of the biological subject;

a film carrier shaped substantially the same as said film backing sheet and attached directly to at least one part of said film backing sheet along said opposite outward surface near the edge, said film carrier being a protective support for said film backing sheet aiding handling of said film backing sheet during application of said dressing to the selected part of the biological subject, said film carrier secured to said film backing sheet and removable therefrom after said dressing is applied to the biological subject;

an adhesive coating covering said subject facing surface of said film backing sheet for adhering to said subject facing surface so that said film backing sheet is sandwiched between said film sheet carrier and said adhesive coating whereby said adhesive coating on said dressing holds said dressing to the selected part of the biological subject as said dressing and film backing sheet are separated, said dressing being adhesively held to the selected part of the biological subject by said adhesive coating with greater adhesive strength than the connection of said demarcation between said dressing and the attachment near the edge of said film backing sheet; and a release sheet for cooperating with said film carrier as a package member and being removably adhered to said adhesive coating prior to application to the biological subject.

2. The delivery system and package of claim 1 wherein said area of attachment forms a continuous frame about said cut line for use in removal of said film carrier and said attached edge of said film backing sheet.

3. The delivery system and package of claim 1 wherein said film backing sheet is substantially transparent in order to facilitate the placement of said dressing on the selected part of the biological subject.

4. The delivery system and package of claim 1 wherein said release sheet has a siliconized surface on its side which meets with the adhesive coating and has indicia printed on the other side for disclosing the use and nature of the self adhering polymer medical dressing.

5. The delivery system and package of claim 1 wherein said demarcation between said dressing and said edge of said film backing sheet is defined by a cut line through said film backing sheet near said attached edge in order to facilitate the placement during application to the biological subject.

6. The delivery system and package of claim 5 wherein said demarcation is immediately adjacent to said area of attachment of said film carrier to said film backing sheet.

7. The delivery system and package of claim 2 wherein said attached edge have a heat sealed interface between said film carrier and film backing sheet which fuses adjoining surfaces.

8. The delivery system and package of claim 7 wherein said cut line includes a portion having greater resistance to separation for use in assisting in the process of removal of said release sheet from said adhesive coating without removal of said dressing from said film carrier.

* * * * *